United States Patent [19]

Troutner

[11] Patent Number: 4,687,464
[45] Date of Patent: Aug. 18, 1987

[54] ZERO INSERTION FORCE SOCKET FOR PHOTOACTIVATION PATIENT TREATMENT SYSTEM

[75] Inventor: Vernon H. Troutner, St. Petersburg, Fla.

[73] Assignee: McNeilab, Inc., Fort Washington, Pa.

[21] Appl. No.: 834,259

[22] Filed: Feb. 27, 1986

Related U.S. Application Data

[63] Continuation-in-part of Ser. No. 665,817, Oct. 29, 1984, Pat. No. 4,573,962.

[51] Int. Cl.[4] .................... A61M 37/00; H01R 13/62
[52] U.S. Cl. .................................... 604/4; 439/260
[58] Field of Search ........................... 604/4–6; 339/74 R, 75 M, 75 MP

[56] References Cited

U.S. PATENT DOCUMENTS

| | | | |
|---|---|---|---|
| 1,950,200 | 3/1934 | Tritle | 339/74 R |
| 4,128,288 | 12/1978 | Zachry et al. | 339/74 R |
| 4,398,906 | 8/1983 | Edelson | 604/6 |
| 4,553,804 | 11/1985 | Lapraik et al. | 339/75 MP |
| 4,575,171 | 3/1986 | Igarashi et al. | 339/75 MP |

*Primary Examiner*—C. Fred Rosenbaum
*Assistant Examiner*—Gene B. Kartchner
*Attorney, Agent, or Firm*—Mark A. Hofer; Richard J. Grochala

[57] ABSTRACT

Automatic operating zero insertion force socket for use in a photoactivatable reagent treatment system wherein photoactivatable agents, in contact with patient blood cells, are irradiated extracorporeally and then returned to the patient.

9 Claims, 5 Drawing Figures

ZERO INSERTION FORCE SOCKET FOR PHOTOACTIVATION PATIENT TREATMENT SYSTEM

This application is a continuation-in-part application of U.S. Ser. No. 665,817, filed Oct. 29, 1984, now U.S. Pat. No. 4,573,962.

FIELD OF THE INVENTION

This invention relates to the field of treating cells with photoactivatable compounds and radiation which activates the compound thereby affecting the cells and specifically, relates to clinically useful patient treatment systems for the extracorporeal treatment of blood cells, especially leukocytes, with UV radiation utilizing an irradiation chamber having electronic memory contacts which mate with a zero insertion force electronic socket for providing electronic communication between the chamber's memory device and the patient treatment system.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness of viability.

Although a number of photoactivatable compounds in the psoralen class are known, 8-methoxy psoralen is presently the compound of choice. An effective radiation for this compound, and many psoralens in gerneral, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems require solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602, describes a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8TS/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicated with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to U.S. Ser. No. 650,602.

To be fully practical, the Taylor device requires a clinically acceptable instrument to house the device and to provide the cells to be treated in an appropriate form. Such an instrument is the object of the inventions described in U.S. Pat. Nos. 4,573,960, 4,568,328, 4,578,056, 4,573,961, 4,596,547, 4,623,328, and 4,573,962, fully incorporated herein by reference. While the instruments described therein work well, it is an object of the instant application to describe improved systems capable of implementing, in advanced fashion, the medical treatment principles first taught by Edelson.

It is another object of the present invention to provide still further improvements in greater patient safety and comfort while reducing treatment time and cost, by utilizing a newly designed disposable irradiation chamber in an appropriate instrument which incorporates a photoactivating light array, more fully described in copending applications U.S. Ser. Nos. 834,258 and 834,256 respectively.

It is yet another object to provide an improved instrument which meets the above criteria while maintaining the positive attributes of the prior system; compactness, mobility, completeness, fully automated and monitored, coupled with ease of operation.

It is further related object of this invention to provide, in contrast to the time consuming batch like processing of the prior system, continuous on-line patient treatment wherein collection, separation, and cell treatment occur simultaneously, thereby reducing treatment time and increasing patient safety and comfort.

It is still another object of the present invention to provide electronic connecting means having increased longevity for receiving in electronic communication memory contact regions associated with irradiation chambers.

BRIEF DESCRIPTION OF THE DRAWINGS

These and still other objects of the invention will become apparant upon study of the accompanying drawings wherein.

SUMMARY OF THE INVENTION

In accordance with the principles and objects of the present invention there is provided an automatic zero insertion force electronic socket for use with photoactivation patient treatment systems for "on-line" extracorporeally photoactivating a photoactivatable agent in contact with patient cells such as blood cells by simultaneously collecting and separating on a continuous basis, blood from a patient while the patient is connected to the apparatus, returning undesired blood portions obtained during separation while the desired portion is photoactivatably treated and thereafter returning the thusly treated cells to the patient. As a result of this novel approach, the treatment system of the instant inventions optimizes and minimizes treatment time by concurrently conducting various aspects of such photoactivation treatment which were previously performed sequentially. More specifically, the apparatus collects and separates blood on a continuous basis as it is withdrawn from the patient and returns unwanted portions to the patient while concurrently energizing the irradiation sources for photoactivating the photoactivatable reagent in contact with the desired blood portion. Following photoactivation, the treated cells may then be facilely returned to the patient utilizing a drip chamber gravity feed infusion line incorporated in the tubing set. The most preferred embodiment of the patient treatment system employs an irradiation chamber having a memory means for providing authenticating and usage information regarding the chamber. The instant invention provides an automatic socket, associated with the patient treatment system, for receiving the memory contacts upon engagement of the chamber in the system. The socket advantageously avoids creating frictional wear surfaces which would otherwise dramatically decrease the life span of the socket during repeated mounting and demounting of the irradiation chamber.

DETAILED DESCRIPTION

Figure 1:
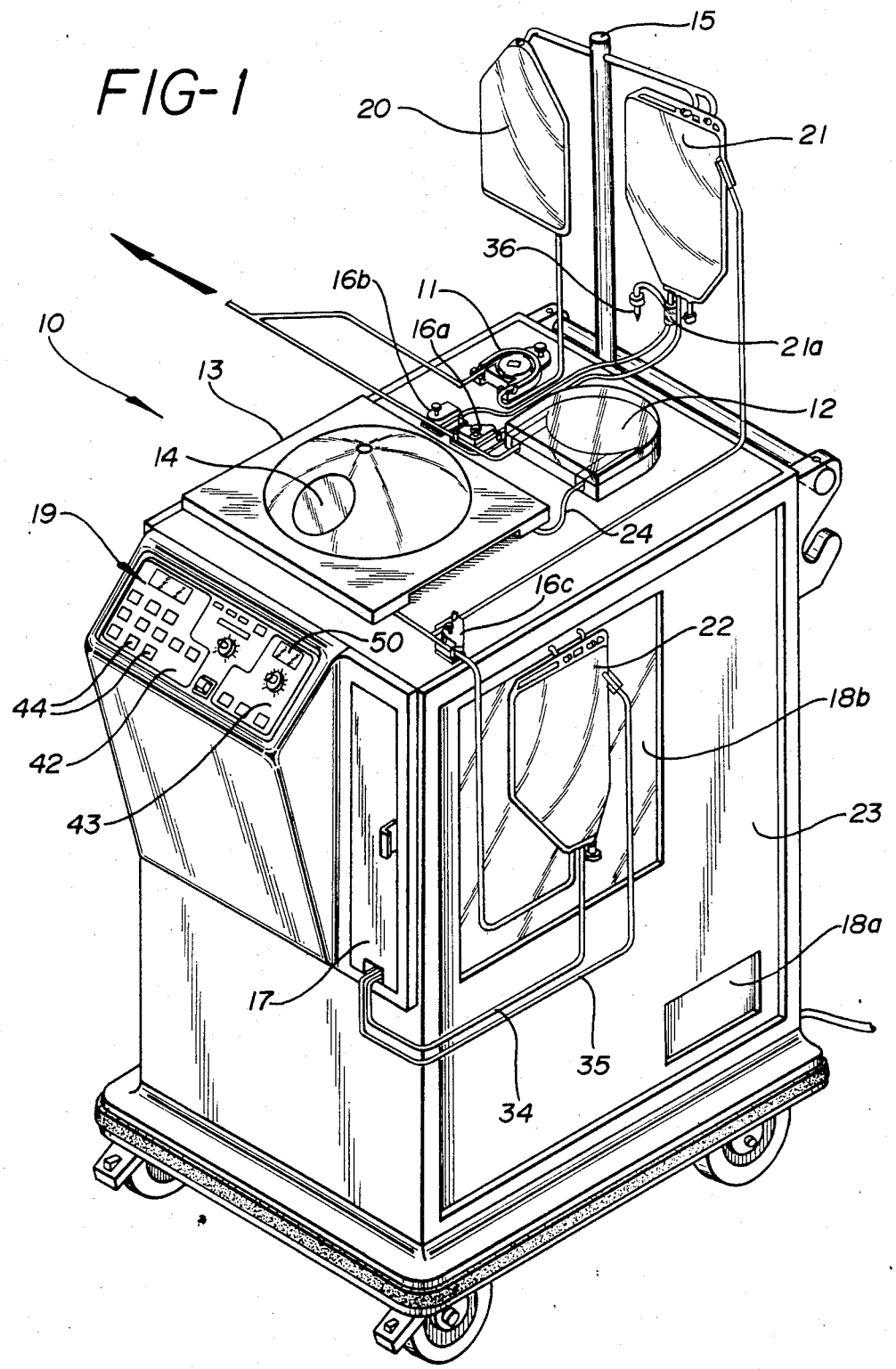
FIG. 1 illustrates a preferred configuration of the system during collection, separation, and treatment.

FIG. 1 shows various aspects of the system developed for extracorporeally treating a patient based in part upon the scientific discoveries of Edelson. While the specific design, construction and operation of the apparatus 10 is the result of a number of separate inventions some of which form the subject matter of previously described issued patents and copending commonly assigned applications including U.S. Ser. No. 834,292 entitled "Concurrent On-Line Irradiation Treatment Process"; U.S. Ser. No. 834,293 entitled "Electronic Device For Authenticating And Verifying Disposable Elements"; U.S. Ser. No. 834,294 entitled "Disposable Temperature Probe For Photoactivation Patient Treatment System"; U.S. Ser. No. 834,303 entitled "Improved Valve Apparatus For Photoactivation Patient Treatment System"; U.S. Ser. No. 834,256 entitled "Light Array Assembly For Photoactivation Patient Treatment System"; U.S. Ser. No. 834,257 entitled "Pump Block For Interfacing Irradiation Chamber to Photoactivation Patient Treatment System"; U.S. Ser. No. 834,260 entitled "Demountable Peristaltic Pump For Photoactivation Patient Treatment System"; and U.S. Ser. No. 834,258 entitled "Irradiation Chamber For Photoactivation Patient Treatment System"; the relevant parts of which are fully incorporated herein by reference, nonetheless it is believed a brief description may be helpful.

The operation of the device and performance of the methods can be divided into two basic phases or modes, depicted in part by FIG. 1. The first phase is shown substantially in FIG. 1 wherein the patient is connected at the point shown, preferably by venipuncture or the like methods well-known and developed to a high degree in the dialysis arts. Patient blood, as it flows to the apparatus 10 (alternately referred to herein as the puvapheresis apparatus or system) is preferably infused, under control of pump 11, with an anti-coagulant agent contained in container 20 hung from stand 15. Control of the flow of patient blood to the remainder of apparatus 10 is controlled largely by clamping means 16a which has the dual function of also controlling flow in the reverse direction as well as flow to return container 21. Clamp 16a acts as an "or" valve.

Normally the blood flows through tubing 24 through blood pump 12 (preferably a roller pump such as that described in U.S. Pat. No. 4,487,558 to Troutner entitled "Improved Peristaltic Pump" and incorporated herein by reference) into continuous centrifuge 13. This continuous centrifuge, available commercially from suppliers such as Dideco, Haemonetics, and others, is preferably capable of continuously separating blood based on the differing densities of the individual blood components. "Continuously", as used herein means that, as blood flows into the centrifuge through line 24, it accumulates within the rotating centrifuge bowl and is separated so that low density components are emitted after a certain minimum volume has been reached within the centrifuge bowl and as additional blood is added. Thus, the continuous centriuge in effect acts as a hybrid between a pure online system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by viewing the uppermost portion of the centrifuge bowl through the centrifuge cover, can detect qualitatively when the centrifuge emits plasma (as opposed to priming solution), leukocyte enriched portions and the remainder, i.e., nonleukocyte enriched portions, including erythrocyte enriched portions. Based on the operator's observations, he or she enters through control panel 19 (specifically via panel portion 42) the identification of the individual blood portions as they are emitted from the centrifuge. This information is entered by keys 44 (e.g. PLASMA, BUFFY COAT or leukocyte enriched portion) on control panel 19, (shown in FIG. 1) and in response thereto, the apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 21.

Once the centrifuge is no longer capable of further separation due to the attainment of its capacity, the operator directs that the bowl be emptied by suitable data key entry on panel 19 and the fluid contents of centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being collected in return container 21.

Between cycles, the fluids, including erythrocytes which have been pumped into return bag 21 are gravity fed back to the patient through a drip infusion operation and controlled by valve 16b. It is preferred that gravity feed be employed rather than pumping the blood back to the patient via pump 12 in order to avoid potential pressurization problems at the infusion insertion site at the patient, and also to avoid foaming or other air related dangers.

As may be already appreciated, when initially set up, the centrifuge bowl and line 24 may be expected to contain sterilized air which is preferably removed by suitable priming operations advantageously accomplished by utilizing the anticoagulation agent in container 20; both the air and a portion of priming solution being collected in container 21.

Also to be noted is the predetermination of the desired leukocyte enriched volumes and plasma volume to be collected within container 22 as well as the number of cycles to be employed to collect same. These volumes are selected largely in accordance with the individual volume capacities of the containers as well as the treatment irradiation chamber to be described later. Accordingly, these volumes are set in order to preferably optimize handling efficiency and to ensure patient safety. For instance, one preferred selection would include the following settings: 250 ml total buffy coat or leukocyte enriched portion and 300 ml of plasma to be collected within container 22. This might require any number of cycles, preferably on the order of three or four, bearing in mind that the more cycles that are selected, the lower the total volume of blood withdrawn from the patient at any one time. If blood collection meets the minimum capacity limits of the centrifuge bowl, the patient's capacity to withstand temporary blood volume depletions and the treatment procedure in general is increased. Further, more cycles will permit more discriminating selection of leukocyte enriched blood as it is emitted from the centrifuge. The buffy coat and plasma volumes as well as the number of cycles are typically physician selected. Accordingly, the controls governing these selections are preferably placed within the apparatus 10, such as behind door 18a where their inadvertent alteration may be advantageously avoided, especially since no operator interaction is normally required with respect to these data inputs.

The leukocyte enriched container 22 is connected via tubing line 34 to the flat plate treatment irradiation chamber behind assembly door 17 with a return line 35 to reservoir container 22.

Figure 2:
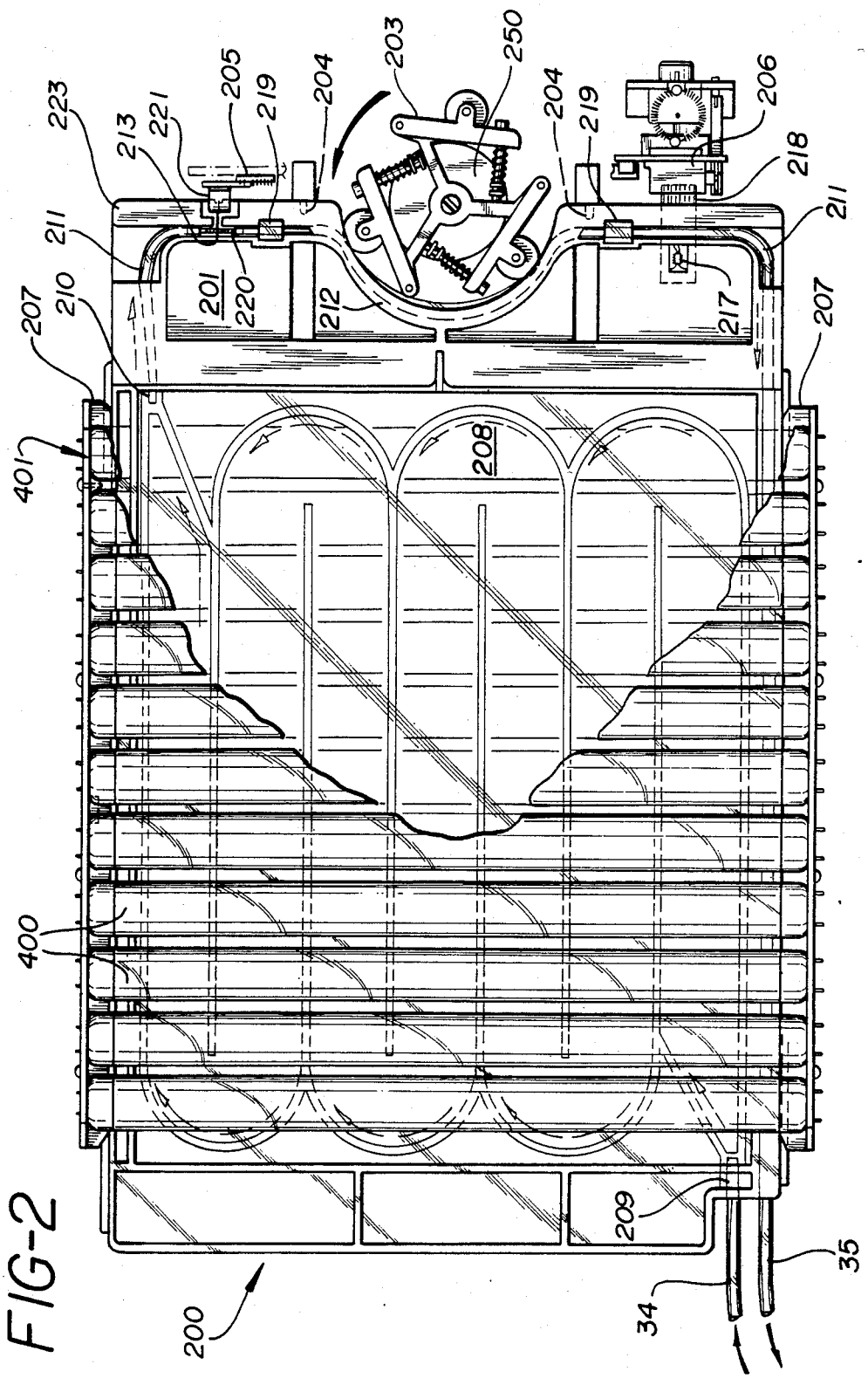
FIG. 2 shows the flat plate irradiation chamber, recirculation peristaltic roller pump, and photoactivating light source array.
Figure 3:
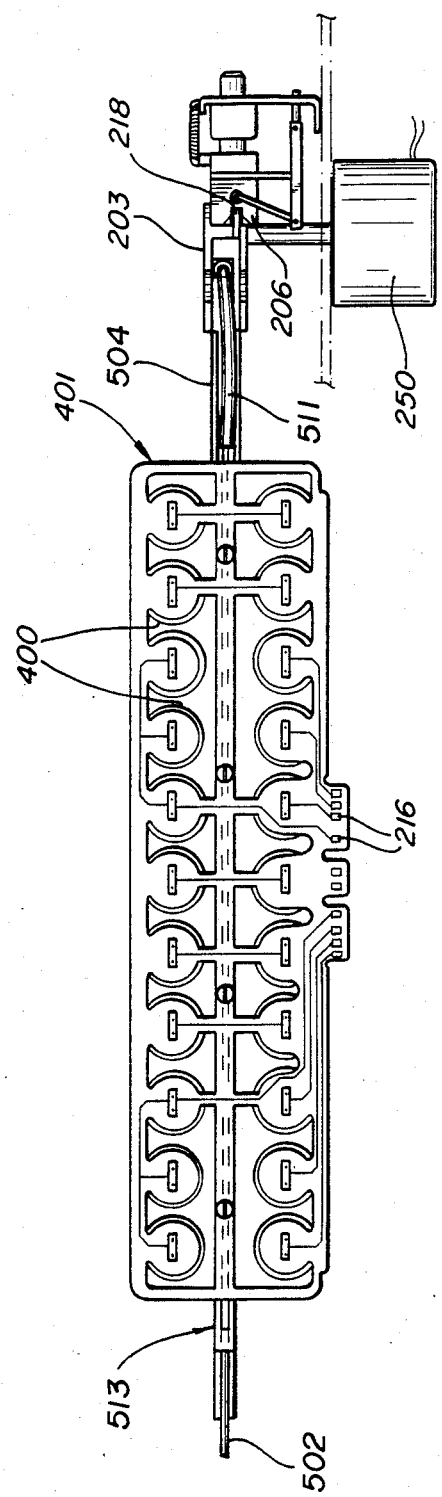
FIG. 3 shows a bottom view of the preferred embodiment depicted in FIG. 2.

Referring now to FIGS. 1, 2, and 3, the leukocyte enriched blood, plasma, and priming solution contained in reservoir 22 (FIG. 1) is delivered through line 34 to the inlet 209 of the flat plate irradiation chamber 200. The fluid flows upward through the serpentine pathway in cavity 208 in the irradiation chamber to the outlet 210. While a serpentine pathway is preferred in order to avoid or minimize stagnant areas of flow, other arrangements are contemplated. Tubing from the outlet 211 passes through the pump block 201 [described in greater detail in U.S. Ser. No. 834,257], affixed to the end of the flat plate irradiator 200, and then connects to return line 35 which returns fluids from the irradiation chamber to container 22.

Recirculation pump rotor 203, which is located internally in the machine (mounting not shown), engages the tubing in the pump block in the semi-circular tract 212 and thereby provides and controls the recirculating flow of fluid, from container 22 up through irradiation chamber 200 and back to container 22. In a preferred embodiment, a metal segment 220 in the tubing line from outlet 211 incorporates a thermocouple 213 [described more fully in U.S Ser. No. 834,294] which permits monitoring of the fluid temperature.

Sterile air initially contained in the irradiation chamber cavity 208 is displaced by entering fluid and stored in the top of container 22. By reversing the rotation of recirculation pump rotor 203, the air stored in container 22 can be pumped back into the outlet 210 of the chamber 200 thereby displacing all fluids back into container 22. Once fluid is initially delivered to container 22, the recirculation pump rotor 203 is energized filling the irradiation cavity 208 and displacing sterile air to container 22. When the irradiation chamber is filled and BUFFY COAT button 44 on panel 19 is pressed, the light array assembly which surrounds the irradiation chamber is energized. Continued operation of the recirculation pump rotor 203 continuously recirculates the leukocyte enriched fluid from container 22 through the chamber for receiving photoactivating radiation from the energized light array assembly 401 (FIG. 3) and back to container 22.

FIG. 3, illustrating the light array assembly 401 from a bottom view, shows two rows, in the most preferred embodiment although one row can be used, of radiation source 400 powered through contacts 216. Such sources are conveniently chosen so that illumination is reasonably constant over the entire irradiation cavity 208

(FIG. 2). Suitable sources include the Sylvania FR15"T8/350BL/HO/180° with 2011 phosphorus bulb which is in the so-called fluorescent tube form. As is apparant from FIG. 3, the irradiation chamber 200 slides between the rows of radiation source 400 so that pump block 201 engages pump rotor 203 driven by motor 250. Other aspects of the radiation array 400 are discussed in U.S. Ser. No. 834,256.

Thus, photoactivation of the leukocyte enriched fluid by irradiation is initiated at the outset and continues through and after the collection and separation process. In the most preferred mode, the light array assembly [described more fully in U.S. Ser. No. 834,256] will comprise sources of ultraviolet radiation, most preferably of the UVA type for activating the photoactivatable agent presently of choice, 8-methoxy psoralen.

The flat plate irradiation chamber treatment module is described more fully in copending application Ser. No. 834,258.

In operation, and with respect to FIG. 2, the exposure time on the right hand portion of the panel 43 is set in accordance with physician determined criteria via knob 41. The central control means of the apparatus 10, calculates and displays (50) via central processing unit and memory stored software, the exposure time remaining at the onset of irradiation treatment and as the treatment progresses. Section 43 of the control panel also includes three operator controlled entry data keys 44 whereby the operator can de-energize the photoactivating light array and stop the recirculation process if desired. Actual photoirradiation treatment preferably commences automatically under control of the central processing unit when fluid is first directed to container 22, continues while leukocyte enriched blood portion from container 22 is pumped through the irradiation chamber back into container 22, and terminates when the preset exposure time has expired. At that time, the light array assembly is de-energized and the recirculation pump reverses emptying the contents of the irradiation chamber 200 into container 22.

Thereafter container 22 is ideally removed to stand 15 (FIG. 1) where it is connected to tube 36, provided on the common drip chamber 21a also associated with return container 21, for reinfusion of the treated blood portion into the patient.

To enhance patient safety and decrease the risk of contamination to the patient blood and blood portions, each time a connection is made or broken, it is preferably only done once. Thus, container 22 would ideally have four connection points or ports; one for the collection of the leukocyte enriched blood portion, two for connection to the flat plate irradiation chamber (feed and return), and the fourth for connection to the drip chamber (21a) for reinfusion of treated blood to the patient.

The control panel 19 of the apparatus 10 is shown with the keyboard entry buttons 44, each ideally having a light which, when lit, preferably indicates the stage of the operation. As will be noted, the keyboard entry buttons 44 are preferably placed in sequential order thereby assisting the operator in learning the system and performing the steps in the correct order. Indeed, the central control microprocessor or computer will preferably be programmed to prevent out of step sequences from being attempted. A visual display indicates the volume of leukocyte enriched blood collected in container 22.

Panel 19 will preferably also contain a power switch, as well as a blood pump speed control whereby the operator may select the speed with which the blood is withdrawn from the patient and pumped through the system during collection. Also preferably included is an alpha-numeric display for indicating the machine's status and identifying alarm conditions throughout system operation. Optional accessory status lights, preferably provided in green, yellow, and red colors, provide at a glance the overall operating status of apparatus 10. Further included is a mute/reset button for quieting an audible alarm activated in the event an alarm condition occurs and operator input is required.

Other features may be readily apparent from the drawings such as the preferable inclusion of casters and caster brakes for enhancing the mobility of the apparatus. Further, side panel 23 will preferably include mechanical means (e.g. hanging pegs and the like) for assisting in the securement of container 22. It may also optionally be outfitted with a transparent or translucent opening 18b in the area beneath container 22 for providing at a glance information regarding the illumination status of the irradiation treatment chamber during the treatment phase. For instance, if the window is of sufficient size, the operator may readily determine that each irradiation source within the treatment chamber is illuminated as desired. Naturally, the material comprising such window is preferably selected in order to contain harmful radiation, if any, within apparatus 10.

The aforedescribed photopheresis blood treatment apparatus is made largely possible by an automated control method for directing the blood portions, derived from the continuous centrifuge, into particular containers. The automated method performs in accordance with preset volume determinations which are manually entered behind panel 18a pursuant to a physician's direction. These predetermined volumes specify the volume to be contained within container 22 by setting forth the volume of plasma and the volume of leukocyte enriched blood portion to be directed thereto. Additionally included within these condition setting parameters is preferably the ability to set forth the number of cycles of blood collection and separation required or desired in order to obtain the desired blood volumes.

The volumes collected are determined in accordance with the blood volume pumped by the blood pump. This may be suitably monitored and communicated to the central control means by specifically monitoring the number of step pulses input to the pump to cause rotation of the blood pump. Typically, 200 pulses results in one revolution. Rotation may also be conveniently monitored such as by attachment of a slotted disk to the shaft and the passage of slots determined by an optical sensor means such as that described in U.S. Pat. No. 4,632,328 (fully incorporated herein) and by monitoring shaft rotation.

The resultant periodic signal may be conveniently correlated with speed and number of rotations by circuit designs well-known in the art. The number of rotations by any of the foregoing methods coupled "with the known volume pumping characteristics of the pump", will provide the necessary information regarding the volume of blood pumped. It will readily be appreciated that the sensors need not be optical but may be electronic or mechanical instead.

In actual operation, a most preferred procedure would be as follows. The operator presses the PRIME CENT. key on control panel section 19 which primes the tubing set, the blood pump, and the centrifuge with the anti-coagulation solution contained in container 20. Displaced sterile air is collected in container 21. When priming solution emerges from the exit of the centrifuge, the operator presses PRIME UV key on control panel section 42 which closes the tubing line to container 21 and opens the tubing line to container 22 by means of valve 16c. Recirculation roller pump rotor 203 is energized to prime the flat plate irradiation chamber and displace sterile air to container 22. The priming process stops automatically after a preset volume of fluid is delivered to container 22.

Blood collection is started by the operator pressing START key on control panel 19. Thereafter, blood is withdrawn from the patient and pumped by the blood pump into the rotating centrifuge. As the blood enters the centrifuge, it displaces the priming solution which emerges first in accordance with its preferably lighter density. This priming solution is automatically directed into container 22 until a preset volume is delivered, after which the emerging solution is redirected to container 21 by means of valve 16c. At some point, the priming solution will be completely displaced from the rotating centrifuge and plasma will begin to emerge. This emergence may be directly observed through port 14 whereupon the operator presses the PLASMA key on control panel 19. Thereafter, the central control means automatically directs the plasma into container 22 by altering valve 16c keeping track of the volume as it does so since the volume entering the centrifuge equals the volume emerging therefrom. This continues until the operator indicates the leukocyte enriched portion, i.e. buffy coat has begun by pressing the respective data entry key in control panel section 42 whereupon, the leukocyte enriched portion continues to container 22, however, the volume so directed is monitored as buffy coat volume. Alternately, if all of the predetermined plasma volume is collected prior to the emergence of the buffy coat, then the central control means automatically diverts, by valve 16c, the emerging plasma fluid stream to container 21. In that instance, upon the emergence of the buffy coat and the keying of the BUFFY COAT data entry switch 44, the central control means diverts the emerging buffy coat into container 22, by means of valve 16c, again keeping track of its volume.

The collection of the buffy coat will preferably continue in accordance with both the predetermined buffy coat volume as well as the number of cycles, another condition predetermined by the physician. If this most preferred embodiment is employed, then a representative example might be as follows. Assume, that the predetermined volume and cycle conditions are set as follows: 350 mls of plasma, 250 mls of buffy coat, and 5 cycles. In each cycle, the apparatus will collect 250/5 or 50 mls of buffy coat before ending the cycle and thereupon emptying the centrifuge bowl and returning all nonleukocyte fluids. predominantly erythrocytes and perhaps excess plasma, to the patient. Prior to the collection of the 50 mls, plasma will emerge from the centrifuge and will be collected in container 22 either until the full 350 mls are collected or, until the buffy coat emerges.

During the next cycle, the central control means will direct the further collection of plasma, if needed, in order to reach the 350 ml predetermined volume and then collect an additional 50 mls of buffy coat. The total volume to be contained within container 22, will then equal 600 mls and would be indicated on display 46 as it is accumulated.

Thus, the instant invention serves to automatically keep track of the volumes as they are collected thereby facilitating the institution of a convenient number of cycles whereby the removal of large blood volumes from the patient is avoided. Not only is patient safety enhanced thereby, but the automated nature of the procedure further increases safety since, in accordance with the programmed conditions supplied to the central control microprocessor, the operator need not attempt to keep track of plasma and leukocyte enriched volumes collected, while still being assured that the final solution for treatment will contain the predetermined and desirable leukocyte concentration.

As described in copending U.S patent application Ser. No. 834,258, there is ideally affixed to the irradiation chamber/pump block assembly a microelectronic memory device which contains coded information that allows the photopheresis patient treatment apparatus to authenticate the disposable irradiation chamber and to verify its suitability for use. To obtain maximum benefit, however, such a memory device depends heavily on the present invention, and in particular, upon an automatic zero insertion force socket for making electronic connection between the memory device and the central control processor of the treatment system.

Figure 4:
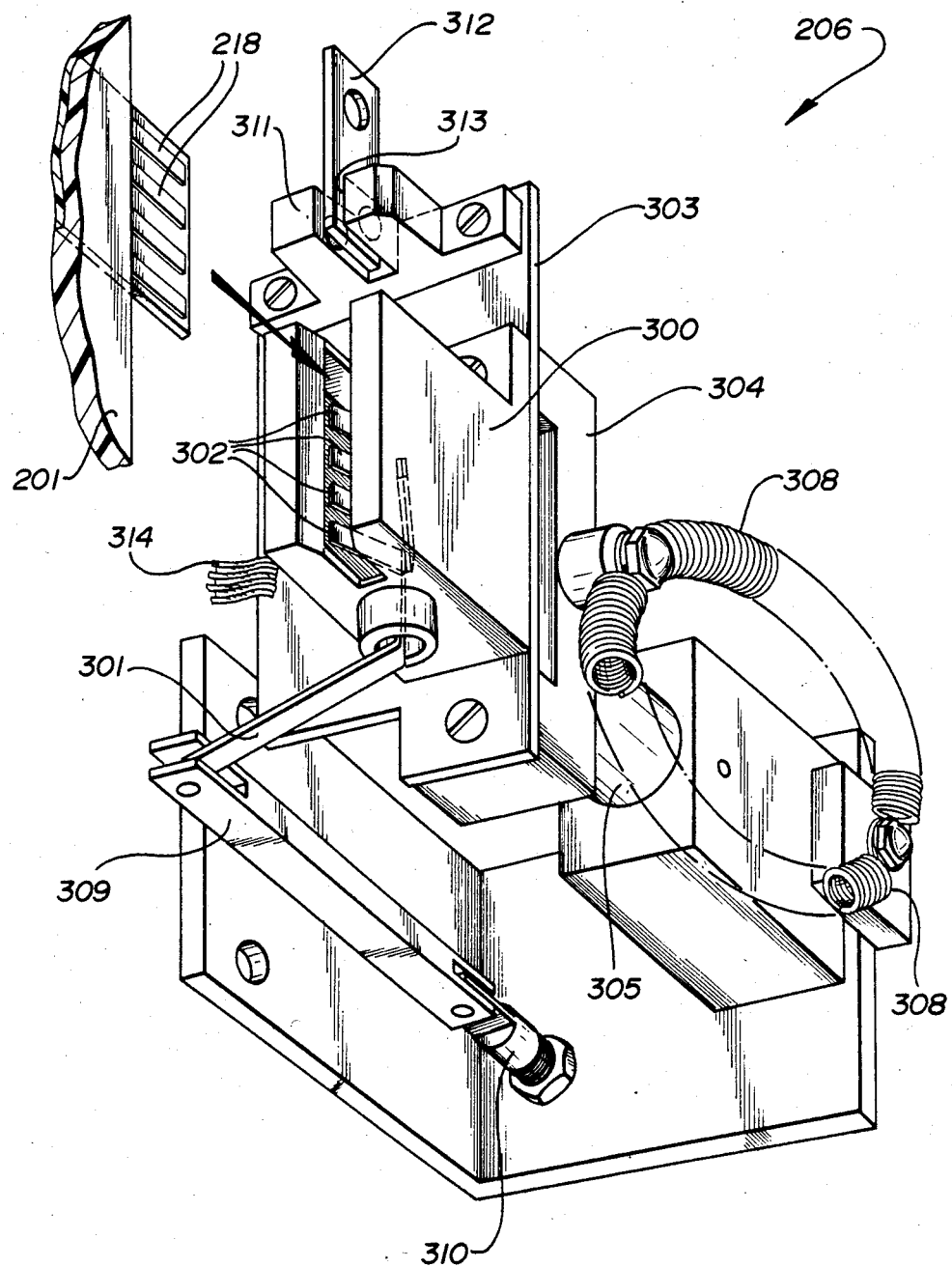
FIGS. 4 and 5 show the most preferred embodiment of an automatic zero insertion force electronic socket of the present invention in perspective and side view respectively.
Figure 5:
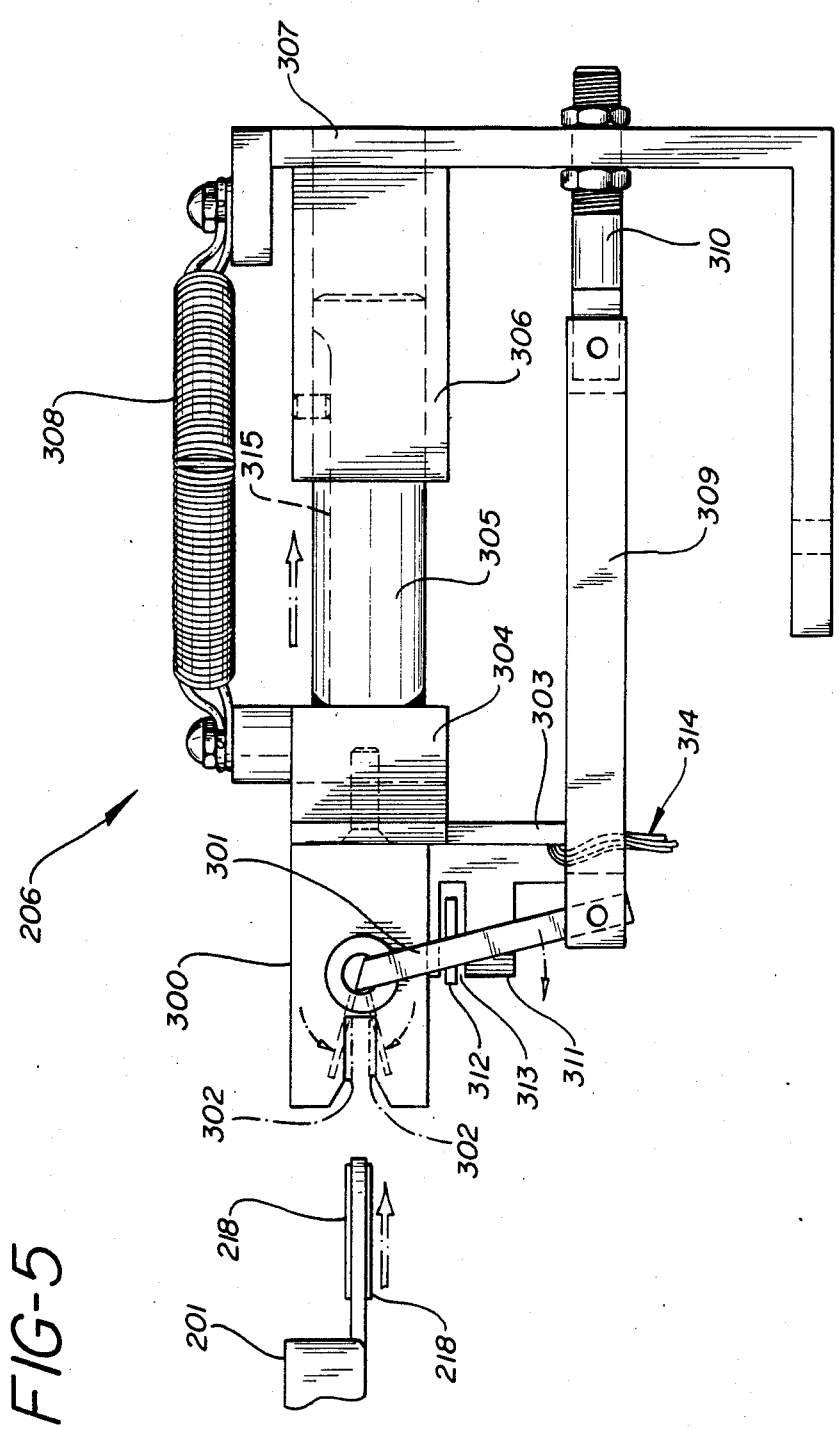

With specific reference to FIGS. 4 and 5, electronic connection to the memory device is made through plated finger contacts 218 on a circuit board affixed to and extending from the leading edge of the partially shown pump block 201. When the irradiation chamber is slid into position, the finger contact circuit board engage the zero insertion force socket device 206, mounted within the instrument while avoiding contact of the finger contacts themselves. Only upon full insertion are the spring contacts 302 of the socket 300 closed to complete the electrical connection. Zero insertion force sockets are known and commercially available with a lever which, upon rotation through an arc of less than 180°, causes spring contacts within the socket to open or close, however, their use in an automatic mode to communicate with a memory device of an irradiation chamber or light source array assembly in a patient treatment system for photoactivating patient fluids has proven to be surprisingly effective and beneficial.

Zero force sockets acquire their name from their mode of action because when the spring contacts are in the open position, the finger contacts of a circuit board can enter freely without encountering any resistance since the socket contacts do not engage the circuit board contacts thus incurring no wear on the contact surfaces. Normally then, the lever arm is rotated to lose the contacts. This operational mode has not been followed in the instant invention. Instead, the spring contact arm is fixably mounted to the patient apparatus and the socket is caused to move as a result of the sliding-mounting movement of the circuit board-finger contacts 218. As shown in FIGS. 4 and 5, lever 301 is fully rotated counter-clockwise and the spring contacts 302 are open prior to mounting of the irradiation chamber. In the present invention, the zero insertion force socket is ideally mounted on a circuit board 303 which in turn is mounted on supporting block 304 connected to shaft 305. Shaft 305 is slidably mounted within a bore in block 306. Keyway slot 315 in the shaft 305 engages a pin in block 306 to prevent rotation. Block 306 is mounted on a bracket 307 which in turn is mounted in the photopheresis patient treatment system (not shown). Constant force springs 308, connected between the bracket 307 and supporting block 304 bias the socket in an outward direction away from the bracket. Socket spring contact operating lever 301 is pivotally connected to a link bar 309 which in turn is pivotally connected to a post 310 fixedly mounted on bracket 307. In the outward biased position, the lever is fully rotated counter-clockwise and the socket spring contacts are open.

In operation, when the irradiation chamber is slidably mounted into position, the finger contacts-circuit board enter the socket freely encountering no frictional contact forces. As the chamber continues to slide toward the bracket 307 and the final installed position as indicated in FIG. 4, the circuit board edge engages the back of the socket thereby causing the socket to move against the bias provided by spring 308 towards the bracket causing lever 301 to rotate clockwise. Upon completion of the mounting operation, lever 301 has rotated sufficiently to cause spring contacts 302 to close and make contact with finger contacts 218 on the irradiation chamber's circuit board. When the irradiation chamber is withdrawn, constant force springs 308 move the socket outward away from bracket 307 causing the lever 301 to rotate counter-clockwise thus opening spring contacts 302. Adjustment of shaft 310 within bracket 307 ideally provides that finger contacts 218 exit the socket only after the spring contacts 302 are fully opened. It is thus apparent that finger contacts 218 can enter and exit the socket with no sliding wear upon the spring contacts 302 within the socket. Further, the spring contacts 302 advantageously close and open automatically as the chamber is slidably mounted into position or withdrawn, respectively.

While the foregoing description has been in terms of a memory device associated with the irradiation chamber, it will be readily appreciated by one skilled in the art that a similar arrangement could be constructed to provide an automatic, zero insertion force socket to electrically communicate with a memory device associated with the light assay assembly described in U.S. Ser. No. 834,256 or with virtually any circuit board.

In addition to the aforementioned features, a solid-state optical switching device 311 may be advantageously mounted on an extension of circuit board 303. Such a device may be of a common commercially available type typically comprising a light source and light detector arranged on opposite sides of a gap such that the presence of a flag 312 within the gap 313 can be detected. In a preferred embodiment of the present invention, a metal flag 312 is fixedly attached to the photopheresis patient treatment apparatus so that it is positioned within gap 313 when the zero insertion force socket 300 is fully extended outward from the bracket 307. When the chamber is mounted into position, socket 300 is moved toward the bracket 307 along with associated optical device 311. Upon completion of its travel, the flag 312 no longer interrupts the light beam in gap 313 thus generating a signal which indicates the movement of the socket and thus presence of a mounted irradiation chamber. Flexible wires 314 convey the electrical signals from the socket and optical device to the central control microprocessor of the patient treatment apparatus.

Upon study of the accompanying figures, and the foregoing description, it will become readily apparent to the skilled artisan that numerous alterations may be made to the foregoing without departing from either the spirit or scope of the instant invention.

What is claimed is:

1. An improved system for inserting a circuit board into electrical contact with a socket, wherein said socket is a zero insertion force socket comprising:
   (a) spring contacts affixed to said socket for electronically communicating with said circuit board;
   (b) means for slidably affixing said socket to a support;
   (c) biasing means for biasing said socket in a first postion wherein said spring contacts are open, said socket adapted to being slidably urged into a second position by said circuit board wherein said spring contacts are closed and in electrical communication with said circuit board; and
   (d) contact operating means pivotably mounted on said support for closing said spring contacts when said socket is slidably urged from the first to the second position to place said contacts into electrical contact with said circuit board and for opening said contacts when said socket is slidably urged from said second position to said first position by said biasing means.

2. The socket of claim 1, wherein the system is a patient treatment system wherein patient fluids, in contact with a photoactivatable agent, are irradiated extracorporeally for photoactivating the agent while said fluid and agent are contained within an irradiation chamber, wherein a light array assembly provides said photoactivating irradiation, and wherein said irradiation chamber and/or light array assembly further comprises an electronic memory device for providing data to said patient treatment system.

3. The socket of claim 1, wherein the means for slidably affixing comprises a shaft, slidably mounted within a bore in said support, said socket being mounted on said shaft.

4. The socket of claim 3, wherein the shaft has a keyway slot for engaging a pin in the system to prevent rotation of the shaft.

5. The socket of claim 3, wherein the means for biasing is at least one spring connecting the socket and shaft to the support.

6. The socket of claim 3, wherein the contact operating means is a lever.

7. The socket of claim 6, wherein the lever is pivotably connected to a link bar, said link bar being pivotably connected to a post fixedly mounted on said support.

8. The socket of claim 1, further comprising a detecting means for detecting the position of the socket.

9. The socket of claim 8, wherein the detecting means comprises an optical detector comprising a light source and a light detector mounted in oppositiion to said light source and forming a gap therebetween whereby movement of said socket from said first position to said second position results in a change in the optical conductivity of said gap whereby a signal is generated indicating movement of the socket from one of said first and second position to the other of said positions.

* * * * *